United States Patent [19]
Haber et al.

[11] Patent Number: 6,157,854
[45] Date of Patent: Dec. 5, 2000

[54] PHOTON IRRADIATION HUMAN PAIN TREATMENT MONITORED BY THERMAL IMAGING

[75] Inventors: Constance Haber, Murrysville, Pa.; Maurice Bales, Lafayette, Calif.

[73] Assignee: Bales Scientific Inc., Walnut Creek, Calif.

[21] Appl. No.: 09/229,689

[22] Filed: Jan. 13, 1999

[51] Int. Cl.$^7$ .......................................................... A61B 5/00
[52] U.S. Cl. ........................... 600/427; 600/474; 600/549; 607/88; 607/100
[58] Field of Search ....................................... 600/427, 474, 600/549, 557; 607/88–90, 100, 102, 108–111

[56] References Cited

U.S. PATENT DOCUMENTS

| | | |
|---|---|---|
| 3,245,402 | 4/1966 | Barnes . |
| 3,900,034 | 8/1975 | Katz et al. . |
| 3,991,744 | 11/1976 | Goodfield . |
| 4,232,678 | 11/1980 | Skovajsa . |
| 4,535,784 | 8/1985 | Rohlicek et al. . |
| 4,622,972 | 11/1986 | Giebeler, Jr. . |
| 4,653,495 | 3/1987 | Nanaumi . |
| 5,000,752 | 3/1991 | Hoskin et al. . |
| 5,024,236 | 6/1991 | Shapiro . |
| 5,178,617 | 1/1993 | Kuizenga et al. . |
| 5,259,380 | 11/1993 | Mendes et al. . |
| 5,358,503 | 10/1994 | Bertwell et al. . |
| 5,445,608 | 8/1995 | Chen et al. . |
| 5,454,807 | 10/1995 | Lennox et al. . |
| 5,464,436 | 11/1995 | Smith . |
| 5,503,150 | 4/1996 | Evans . |
| 5,849,026 | 12/1998 | Zhou et al. . |

FOREIGN PATENT DOCUMENTS

| | | |
|---|---|---|
| 2371935 | 7/1978 | France . |
| 2591902 | 6/1987 | France . |
| 1266540 | 10/1986 | Russian Federation . |
| 1641267 | 4/1991 | Russian Federation . |
| 1703058 | 1/1992 | Russian Federation . |
| 2208803 | 9/1991 | United Kingdom . |

OTHER PUBLICATIONS

Goodman, P.H. et al., "Decision Support Technology: Quantitative Analysis of Infrared Images," *Termology*, 1986—1(4):249[#3956].

Kahn, MD, F. et al., "Lasers Heal," *Dynamic Chiropractic*, (three pages) Nov. 16, 1996.

*Primary Examiner*—Ruth S. Smith
*Attorney, Agent, or Firm*—Tarolli, Sundheim, Covell, Tummino & Szabo L.L.P.

[57] ABSTRACT

Photo illumination of sites along a nerve supplying a painful region is conducted one at a time until a thermal image of that region or one related to it shows a significant change in temperature, at which time the treatment is terminated. If it is an extremity (hand or foot) that is has pain symptoms, one extremity is treated by exposing its nerve sites to photo illumination while the other extremity is observed by a thermograph instrument. Use of the thermal image as a feedback technique allows the treatment to be terminated as soon as the favorable temperature change takes place.

6 Claims, 2 Drawing Sheets

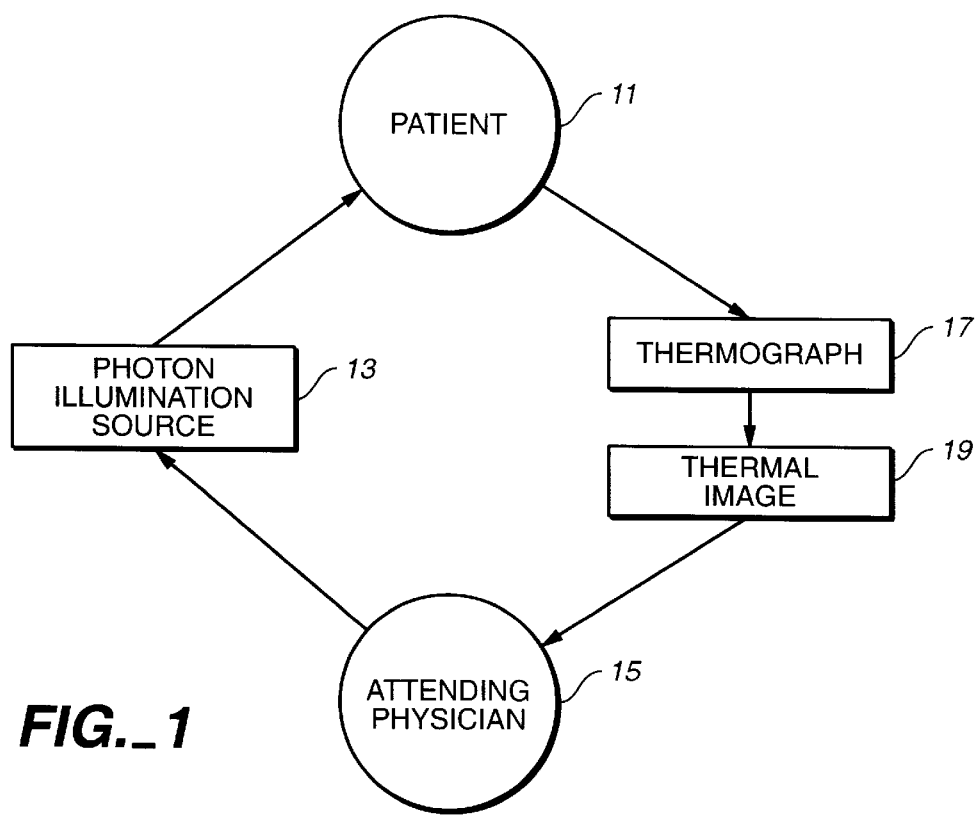
FIG._1
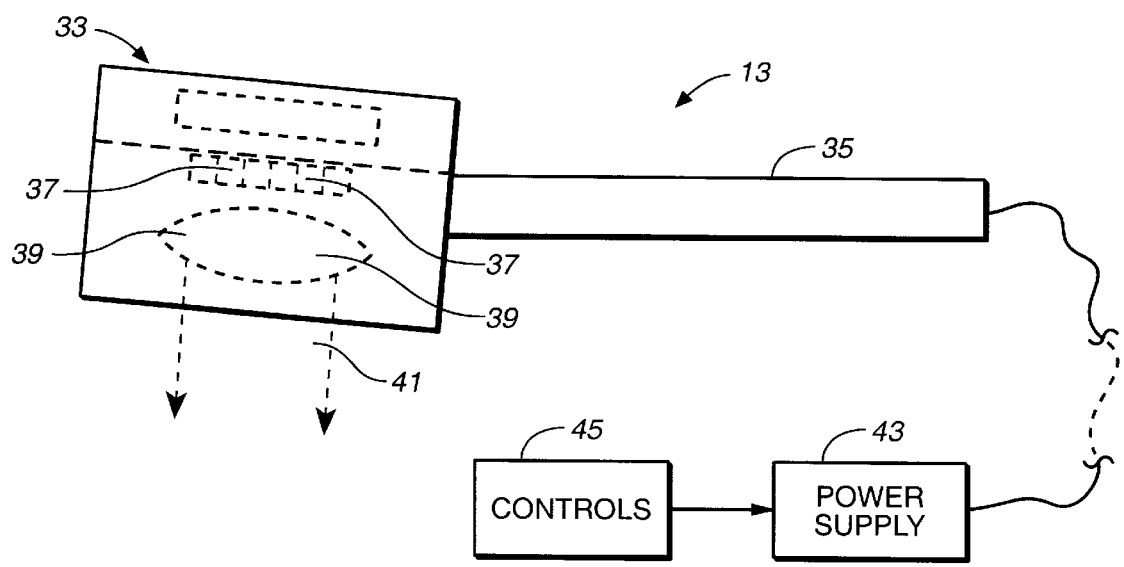
FIG._3

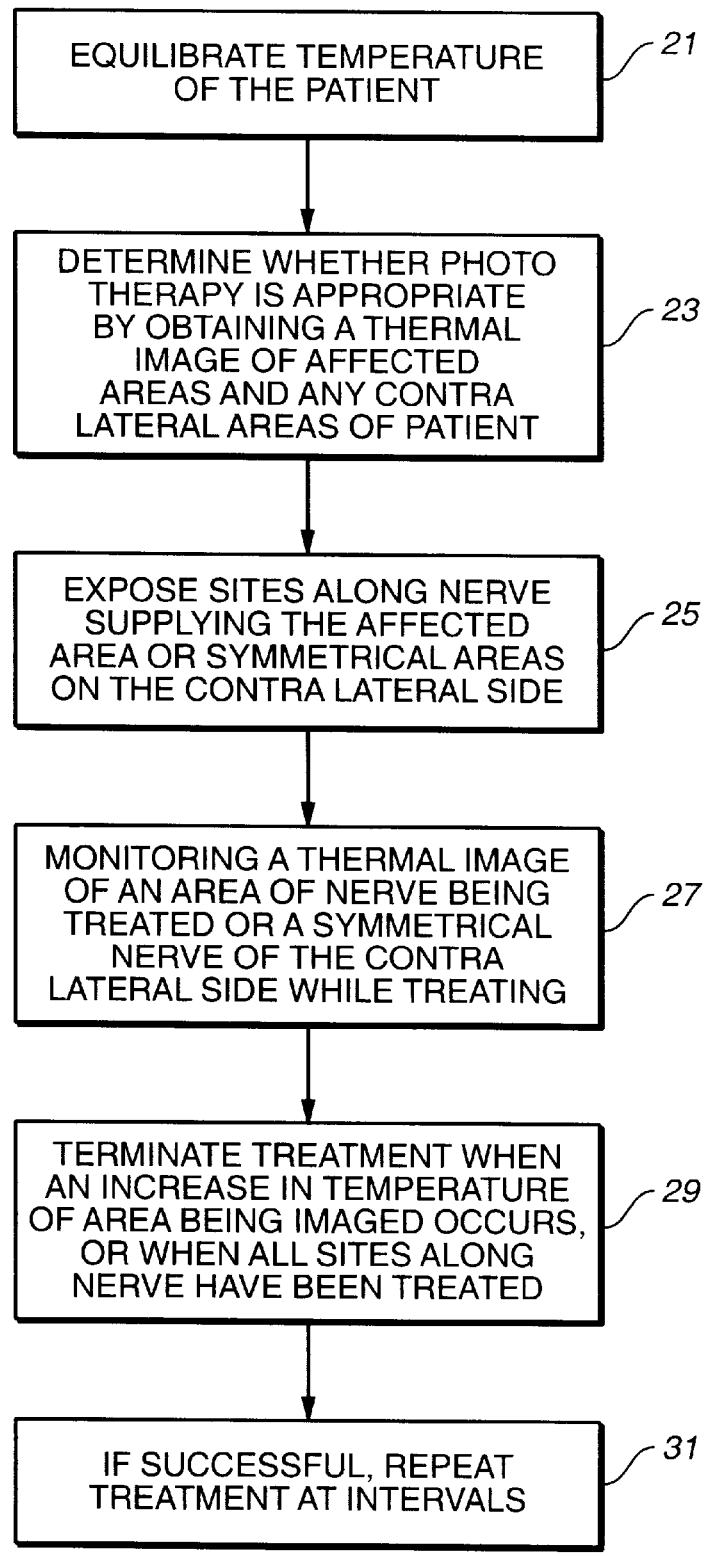
FIG._2

PHOTON IRRADIATION HUMAN PAIN TREATMENT MONITORED BY THERMAL IMAGING

BACKGROUND OF THE INVENTION

This invention relates generally to techniques of reducing or eliminating pain by application of infrared irradiation, and, more specifically, to methods and apparatus for monitoring the effects of such treatment as it is being conducted.

Infrared irradiation and low energy lasers are widely used as treatment devices for a number of medical conditions. Photons of energy are delivered to tissue below the surface of the skin without causing adverse effects of superficial heating of the skin. Raising the temperature of internal damaged tissue is thought to promote healing by increasing blood flow and stimulating the immune system. Nerves have also been treated by directing penetrating radiation through the skin at acupuncture sites in order to treat suspected causes of chronic pain. The primary technique for determining whether such treatment has been successful is to evaluate reports of the patient as to whether the pain has subsided.

It is an object of the present invention to provide improved techniques for evaluating and treating nerves with penetrating infrared irradiation in order to normalize their function thereby alleviating chronic pain.

It is another object of the present invention to provide improved techniques for determining the effect of the treatment.

SUMMARY OF THE INVENTION

These and other objects of the present invention are accomplished, briefly and generally, by treating nerves at known acupuncture sites with electromagnetic radiation, preferable non-coherent electromagnetic radiation in the infrared range of the spectrum. A large number of conditions that cause pain are able to be treated in this manner. Monitoring the treatment while it is occurring is accomplished by observing live thermal images of the temperature patterns of the afflicted area, which responds when the condition has been successfully treated by the photon stimulation.

Treatment sites along a nerve supplying the afflicted region of pain are treated one at a time, beginning with the site closest to the region and then proceeding away from the region along the identified nerve. As soon as the monitored thermal image changes in a manner to indicate the nerve has responded to stimulation, the procedure is terminated, continued treatment being unnecessary. This real time feedback to the attending physician of the effect of the treatment provides him or her with objectification of response to stimulation and eliminates unnecessary additional treatments. Without such feedback, the attending physician must complete applying infrared irradiation to all chosen sites along the specific nerve and then wait for a subjective report from the patient as to whether the pain has decreased or gone away. Although the unnecessary further treatments are not known to cause any harm, they would extend the duration and cost of the treatment. It is usually desirable to repeat the treatment several times, at intervals of at least several hours to several days. During such repeated treatments, the attending physician need expose only those sites determined by the thermal imaging of the first treatment to be sufficient.

One specific application of the present invention is in the treating of an extremity (hand or foot) in which the patient is experiencing pain, such as the continuous diffuse limb pain of complex regional pain syndrome (CRPS). In this case, the nerve sites of one of the painful extremities and the other contralateral extremity is treated and the corresponding region of the extremity not being treated is imaged by high-resolution telethermographic instrumentation. As soon as the attending physician notes that the temperature of the monitored extremity has changed, treatment of the other extremity may be terminated. No other sites along an identified nerve are treated after the temperature change takes place.

Additional objects, advantages and features of the various aspects of the present invention will become apparent from the following description of its preferred embodiments, which description should be taken in conjunction with the accompanying drawings.

BRIEF DESCRIPTION OF THE DRAWINGS

FIG. 1 conceptually illustrates a patient's treatment process with a thermal feedback image;

FIG. 2 is a flow diagram outlining the steps of carrying out treatment according to FIG. 1;

FIG. 3 illustrates the photon illumination source of FIG. 1.

DESCRIPTION OF THE PREFERRED EMBODIMENTS

The diagram of FIG. 1 very broadly illustrates the treatment procedures of the present invention. Selected sites of a patient 11 are treated with infrared irradiation from an illumination source. The radiation is within the infrared portion of the electromagnetic energy spectrum and is approximately one micron in wavelength. The wavelength is chosen to penetrate into tissue through the skin. Although a laser can be used as the illumination source, it is preferable to use a non-coherent infrared source having a small wavelength spread. Such a source is easier to control and use than a laser; this is less likely to be the inadvertent cause of any damage to the patient.

A thermograph 17 is positioned to receive a thermal image 19 of an appropriate area of the patient 11. The thermograph 17 may be used to constantly display that image in real time, on its video color monitor, or periodically provide a thermal image after each exposure, either on its monitor or in printed form, after each site exposure of the patient. In either case, lines of constant temperature are preferably superimposed on the patient image, and the image is shaded with different colors to show regions that are at the same temperature. Such a thermograph is available from Bales Scientific, Inc., of Walnut Creek, Calif. Although any infrared imaging device would allow the attending physician to determine when the temperature of the imaged patient area changes, a high-resolution telethermographic apparatus is preferred.

The treatment procedure is outlined generally in the flowchart of FIG. 2. A first step 21 is to place the patient in a room of a constant temperature, until the patient's temperature is stable. A next step 23 is to confirm that the procedure is likely to benefit the patient. In addition to hearing the patient's description of his or her pain symptoms, a thermal image is taken of at least the affected region of pain. Irregular isothermal contours in the image indicate a condition that can potentially be treated by the present invention. If the affected region is on a limb (arm or leg) or an extremity (hand or foot) a thermal image of the corresponding region on the contralateral limb or extremity also provides useful information. If the thermal images of the affected and contralateral regions show significantly different temperature distributions, this is further evidence of a condition that is treatable by photon illumination techniques of the present invention.

In a step 25, acupuncture sites along a nerve that supplies the affected region are treated with infrared irradiation by the source 13, one at a time, beginning with the site furthest into the affected region, or nearest to it, if there is no site identified to be within the affected region. If the physician chooses, the contralateral region could be treated initially to determine the patient's sensitivity.

Simultaneously with the treatment being performed, or at least after each site exposure, a thermal image is acquired and reviewed by the attending physician, as indicated by a step 27. Both treated and contralateral sites are evaluated and reviewed. Contralateral sites also exist throughout the body in regions other than in a limb or extremity. For example, a site of pain on the back a distance from the spine has a contralateral site the same distance on the other side of the spine. However, in cases where no contralateral region exists, the thermal image is taken along the same nerve being treated but a distance from the affected region. In either case, the thermal image can alternatively be taken of the region being exposed to the infrared irradiation after each site exposure but this is not preferred.

As soon as the attending physician observes a significant change in the temperature of the monitored region, treatment is terminated, as indicated by a step 29. This indicates successful treatment. If, on the other hand, no such temperature change is noted after all the sites along the identified nerve have been treated, it is concluded that the treatment is not being effective and no further such treatment is required.

But if the treatment is successful, it is usually desirable to repeat exposure of the same sites in each of one, two, or even more subsequent sessions, as indicated by a step 31. In an extreme case, these sessions may be had with only a few hours between them. In the more usual case, a treatment session is held every other day or so. The subsequent treatments are usually limited to treating the same sites as during the first treatment. Thermal imaging need not always be done in real time during the subsequent treatment sessions since it has already been determined, in the first session, the site exposure pattern that brings about positive results. But a thermal image is generally desirable to have at the end of each session in order for the attending physician to determine when a desired level of thermal equilibration has been reached in the affected region, or between the affected and contralateral regions.

By using thermal imaging in real time during at least the first treatment, the effectiveness and objectivity of the treatment are established. This is better feedback than can be provided by the patient alone, who may not experience a reduction of end of his or her pain symptoms for some time after the treatment. Even if there is an earlier change in the symptoms, the patient's report is subjective in nature and may not be accurate.

A preferred form of illumination 13 is shown in FIG. 3. A housing 33 is attached to an end of a handle 35. A two dimensional array of infrared emitters 37 is carried within the housing 33. The wavelengths included in the radiation emitted are distributed around 950 nanometers, in a specific example. An optical system 39 which includes a diode mosaic array gathers diverging radiation from the emitters and forms an approximately collimated beam 41. For the applications described herein, the beam 41 is made to be about one inch in diameter. This is large enough to be able to treat each individual nerve site without having to be precisely aligned with and directly pointed to the site. The emitters 37 are electrically driven by a power supply 43 that includes controls 45. The controls 45 can be implemented in a manner to make it easy for the attending physician to set the duration and level or each radiating exposure. In some circumstances, it may also be desirable to modulate the intensity of the radiation during the exposure.

It is believed that the photon treatment functions by improving communication between sensory and sympathetic nerves that have become altered. Without proper communication, it is opined, the sympathetic nerves cause blood vessels to constrict and keep a region of the body from receiving an adequate flow of blood. The lack of adequate blood flow causes perpetuation of the chronic pain symptoms that results in the patient seeking treatment. It is believed that communication between the sensory and sympathetic nerves are reestablished as a result of the photon energy being absorbed by nerve cells that communicate between the two. Since the treatment technique is not invasive, it is very safe for the patient and operator.

Dramatic results have been obtained during treating complex regional pain syndrome (CRPS) in the hands or feet. The painful extremity and the contralateral one are initially thermally imaged. If the images show an average temperature difference between the extremities of 0.5° or more, the photon treatment will likely follow. The acupuncture sites of the warmest of the two extremities are treated one site at a time with infrared irradiation. The other extremity is viewed with the thermograph instrument. As soon as a significant change in the temperature of the other extremity is observed from the thermal image, the treatment is terminated. The same set of sites is treated about two days later and again about two days after that. The subsequent treatments are primarily designed to prevent regression.

Although the various aspects of the present invention have been illustrated with respect to its preferred embodiments, it will be understood that the invention is entitled to protection within the scope of the appended claims.

It is claimed:

1. A method of treating a human patient to relieve pain in an area of the patient's body, said method comprising the steps of:
    illuminating with penetrating infrared radiation at least one site of the patient's body along a primary nerve distribution associated with said at least one site;
    simultaneously monitoring a thermal image of a contralateral site of the patient's body; and
    terminating illumination of said at least one site in response to the thermal image showing alteration of the temperature of said contralateral site.

2. The method of claim 1 wherein the penetrating infrared radiation is non-coherent.

3. The method according to claim 2 wherein the penetrating infrared irradiation is produced by a diode mosaic array.

4. The method according to claim 1 wherein said at least one site is innervated.

5. A method of treating a human patient for pain in an affected extremity, said method comprising the steps of:
    irradiating with penetrating infrared radiation, one at a time, sites along a nerve associated with either the affected extremity or a corresponding contralateral extremity;

simultaneously monitoring a thermal image of the extremity not being irradiated;

observing after the individual exposures whether the thermal image shows a change in temperature;

if a predetermined temperature change is observed from the thermal image, terminating irradiation of further nerve sites; and if a predetermined temperature change is not observed from the thermal image, continuing to expose nerve sites until a sufficient quantity of nerve sites have been exposed to produce a predetermined change in temperature or until a maximum number of such nerve sites have been exposed.

6. The method of claim 5 further comprising the steps of:

obtaining initial thermal images of both the affected extremity and the contralateral extremity prior to said step of irradiating sites along a nerve; and deciding, based on the initial thermal images, whether to irradiate the affected extremity or the contralateral extremity.

* * * * *